United States Patent
Laufer et al.

(10) Patent No.: US 9,464,256 B2
(45) Date of Patent: Oct. 11, 2016

(54) METHODS FOR PRODUCING OIL FORMULATIONS BY MEANS OF CERTAIN CARBODIIMIDES

(71) Applicant: Rhein Chemie Rheinau GmbH, Mannheim (DE)

(72) Inventors: Wilhelm Laufer, Ellerstadt (DE); Armin Eckert, Oberhausen-Rheinhausen (DE); Siegfried Kuenzel, Heddesheim (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 14/888,950

(22) PCT Filed: May 6, 2014

(86) PCT No.: PCT/EP2014/059217
§ 371 (c)(1),
(2) Date: Nov. 4, 2015

(87) PCT Pub. No.: WO2014/180833
PCT Pub. Date: Nov. 13, 2014

(65) Prior Publication Data
US 2016/0083673 A1   Mar. 24, 2016

(30) Foreign Application Priority Data

May 7, 2013 (EP) .................................. 13166762

(51) Int. Cl.
| | | |
|---|---|---|
| C11B 5/00 | (2006.01) | |
| C10M 177/00 | (2006.01) | |
| C10M 133/22 | (2006.01) | |
| C07C 67/62 | (2006.01) | |
| C10M 169/04 | (2006.01) | |

(52) U.S. Cl.
CPC ............... *C11B 5/005* (2013.01); *C07C 67/62* (2013.01); *C10M 133/22* (2013.01); *C10M 169/04* (2013.01); *C10M 177/00* (2013.01); *C10M 2203/1065* (2013.01); *C10M 2207/2835* (2013.01); *C10M 2207/401* (2013.01); *C10M 2215/14* (2013.01); *C10N 2230/66* (2013.01); *C10N 2240/10* (2013.01); *C10N 2240/12* (2013.01); *C10N 2240/201* (2013.01); *C10N 2240/40* (2013.01); *C10N 2250/10* (2013.01); *C10N 2270/00* (2013.01)

(58) Field of Classification Search
CPC .. C11B 5/005; C07C 67/62; C10M 1336/22; C10M 169/04; C10M 177/00
USPC .......................................................... 554/5
See application file for complete search history.

(56) References Cited

U.S. PATENT DOCUMENTS

| | | | | |
|---|---|---|---|---|
| 3,152,131 A | * | 10/1964 | Heberling, Jr. ...... | C07D 213/74 502/167 |
| 3,346,496 A | * | 10/1967 | Lohmar ................... | C10M 1/08 252/401 |
| 5,614,483 A | | 3/1997 | Fessenbecker et al. | |
| 2007/0021311 A1 | * | 1/2007 | Poirier ................ | C10M 169/04 508/234 |
| 2008/0033201 A1 | | 2/2008 | Hof et al. | |
| 2015/0133623 A1 | | 5/2015 | Laufer et al. | |

FOREIGN PATENT DOCUMENTS

| | | | | |
|---|---|---|---|---|
| CH | EP 2138556 A1 * | 12/2009 | .......... | C10M 129/00 |
| DE | EP 0705898 A2 * | 4/1996 | .......... | C10M 133/22 |
| DE | 10349168 A1 * | 6/2005 | ............. | C08G 18/42 |
| DE | 102009001130 A1 * | 8/2010 | ............... | H01B 3/20 |
| JP | EP 0647701 A1 * | 4/1995 | .......... | C10M 133/22 |
| WO | WO 0022074 A1 * | 4/2000 | .......... | C10M 141/00 |

OTHER PUBLICATIONS

International Search Report for International Application No. PCT/EP2014/059217, dated Aug. 18, 2014, 4 pages.

* cited by examiner

*Primary Examiner* — Deborah D Carr

(57) ABSTRACT

The present invention relates to a novel method for preparing stabilized oil formulations by means of certain carbodiimides.

11 Claims, No Drawings

METHODS FOR PRODUCING OIL FORMULATIONS BY MEANS OF CERTAIN CARBODIIMIDES

The present invention relates to a novel method for preparing stabilised oil formulations by means of certain carbodiimides.

A series of base oils and lubricant base substances, e.g. triglycerides, synthetic carboxylic esters, phosphoric acid triesters, olefin-dicarboxylic acid copolymers and silicone oils, are attacked by water or oxidizing agents forming acidic cleavage products and alcohols. These acidic cleavage products are a measure of the degree of decomposition. They can be quantitatively specified in the form of the acid number such that these serve as a measure of the degree of ageing of the lubricant oils.

The presence of acids or acidic cleavage products accelerates the hydrolysis autocatalytically. Since water is always present in low amounts under industrial conditions, the service life of lubricants is limited accordingly. As described in DE 4435548 A1, the addition of oil-soluble carbodiimides can effectively prevent hydrolytic decomposition. The methods described in the prior art for preparing oil formulations stabilised with carbodiimides have the disadvantage, however, that solid carbodiimides are used. These must first be melted and subsequently be stirred into the warmed oil formulations. This procedure is very inconvenient and moreover uneconomic. Ideally, the carbodiimides should be stirred in at low temperatures. In addition, in this process the carbodiimides tend to eliminate toxic isocyanates and isocyanates volatile at the temperatures used.

The object of the present invention, therefore, consists of providing methods not having the disadvantages of the prior art.

It has now been found, surprisingly, that oil formulations can be stabilised in a simple manner by the method according to the invention and thereby rendering this process economic for the lubricant industry. Furthermore, the method according to the invention also makes a significant contribution to improving occupational hygiene and environmental protection.

The present invention therefore relates to a novel method for preparing oil formulations, in which at least one carbodiimide of the formula (I)

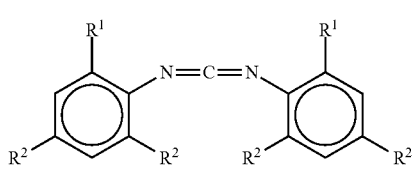

where
$R^1=CH_3$ or $CH(CH_3)_2$ and $R^2=H$ or $CH(CH_3)_2$,
is added to at least one oil at temperatures of 10-40° C., preferably 15-30° C.

In a particularly preferred embodiment of the invention, $R^1=CH_3$ and $R^2=H$.

In a further preferred embodiment of the invention, $R^1=R^2=CH(CH_3)_2$.

The carbodiimides of the formula (I) are commercially available compounds obtainable from, for example, Rhein Chemie Rheinau GmbH under the trade names Stabaxol® or Additin®.

Particular preference is given to bis-o-tolylcarbodiimide, commercially available from Rhein Chemie Rheinau GmbH under the trade name Stabaxol®MTC.

In the context of the invention, the oil preferably takes the form of mineral oils, particularly preferably low-sulphur naphthenic base oils and/or natural fats, oils or waxes,—triglycerides, preferably soybean oil, rapeseed oil or sunflower oil and also synthetically prepared esters, for example, starting from methanol, 2-ethylhexanol, glycol, glycerol, trimethylpropanol (TMP), pentaerythritol or neopentyl glycol esterified with, e.g. stearic acid, oleic acid, adipic acid, terephthalic acid and trimellitic acid.

In a preferred embodiment of the present invention, the oil is a trimethylolpropane ester (TMP) of the general formula (II)

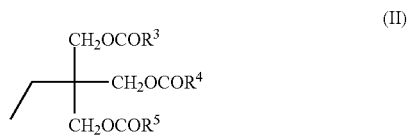

Suitable trimethylolpropane esters are known from the German patent application DE 10 2004 025 939 A. In the general formula (II) above, the residues $R^3$, $R^4$ and $R^5$, which may each be the same or different, have a linear or branched alkyl group having 5 to 22 carbon atoms. In a further preferred embodiment of the present invention, the residues $R^3$, $R^4$ and $R^5$, which may each be the same or different, define a linear or branched alkyl group having 7 to 18 carbon atoms.

Particular preference is given here to trimethylolpropane trioleate (TMP oleate).

With regard to the synthetically prepared esters based on methanol, rapeseed oil methyl ester is preferred.

In a further preferred embodiment of the invention, a mixture of oils is used.

The oil formulations stabilised by the method according to the invention may also further comprise customary additives for this field of application. For example, these may be antioxidants or metal deactivators.

In a further embodiment, the oil formulation therefore comprises in addition 0.005 to 1.0% by weight of an antioxidant and/or 0.01 to 2.0% by weight of a metal deactivator, based in each case on the oil formulation.

The preferred amount of antioxidant is between 0.1 and 0.5% by weight and particularly 0.1-0.2% by weight, based on the oil formulation.

The preferred amount of metal deactivator is between 0.1 and 1.0% by weight and particularly 0.1-0.2% by weight, based on the oil formulation.

The antioxidants are preferably selected from the group consisting of bishydroxytoluene, hydroquinone, 4-tert-butylcatechol, naphthol, phenylnaphthylamines, diphenylamines, phenolic thioethers, tocopherols and mixtures of the substances listed.

The metal deactivator is preferably selected from the group consisting of organic heteroatom compounds, particularly preferably triazoles, tolyltriazoles, dimercaptothiadiazoles and mixtures of the substances listed.

To stabilise the oil formulations prepared in accordance with the invention, concentrations of 0.05-2% by weight, preferably 0.1-1% by weight and particularly preferably 0.2-0.5% by weight of carbodiimide are used, based on the oil formulation.

The carbodiimide is preferably added in a mixing or storage vessel, particularly preferably directly in the container, preferably in a drum or container.

In a preferred embodiment of the invention, the carbodiimide is poured into the oil or pumped in via a pipe. Mixing generally already occurs while metering in, which can be enhanced, however, by stirring units such as paddle stirrers, helical stirrers or anchor stirrers, dispersants, drum or container stirrers.

In a further preferred embodiment of the invention, the carbodiimide is charged in the mixing or storage vessel, particularly preferably directly in the container, preferably in a drum or container, and the oil subsequently poured in. On pouring in the oil, generally an adequate mixing already occurs.

The invention further relates also to oil formulations prepared by the method according to the invention and also the use thereof as process oils, fuels, heat transfer oils, motor oils, fats, metalworking fluids, turbine and transformer oils.

The examples which follow serve to illustrate the invention but have no limiting effect.

WORKING EXAMPLES

In the examples which follow, the following substances were used:
SXL MTC=Stabaxol®MTC, a liquid carbodiimide of the formula (I) where $R^1$=CH$_3$, $R^2$=H from Rhein Chemie Rheinau GmbH.
SXL I Liq=Stabaxol® I Liq, a carbodiimide of the formula (I) where $R^1$=$^2$=CH(CH$_3$)$_2$.
SXL I=Stabaxol® I, a solid monomeric carbodiimide based on 2,6-diisopropylphenyl isocyanate from Rhein Chemie Rheinau GmbH.
TMP oleate=Synative® ES TMP 05 from BASF SE.
Rapeseed oil methyl ester (RME) from ADM Hamburg AG.

Example 1

The "Beverage bottle test" ASTM D 2619 is part of internationally recognised oil formulation specifications and is used to test the hydrolytic stability of liquids. The increase in the acid number is monitored as a measure of the hydrolytic stability.

Test Conditions:
75 ml of test oil (rapeseed oil methyl ester), abbreviated as RME below
25 ml of distilled water
temperature: 95° C.
Evaluation Criteria as a Function of Time (h):
acid number (AN) of the oil phase (mg KOH/g)
acidity of the water phase (mg KOH/25 ml).

TABLE 1

For the inventive examples, 0.5% by weight or 1% by weight of SXL MTC was stirred into the rapeseed oil methyl ester at 30° C. over 1 hour, For the comparative examples, the temperature had to be increased to 80° C. in order to melt the SXL I and thus to be able to dissolve it in the oil. Accordingly, 0.5% by weight or 1% by weight of SXL I was stirred in at 80° C. over 1 hour.

| ASTM D 2619 | RME (C) | RME plus 1% SXL I (1 h, 80° C.) (C) | RME plus 0.5% SXL I (1 h 80° C.) (C) | RME plus 0.5% SXL MTC (1 h, 30° C.) (I) | RME plus 1% SXL MTC (1 h, 30° C.) (I) |
|---|---|---|---|---|---|
| Acidity (mg KOH/g) | | | | | |
| 96 h | 2.18 | 0.47 | not measured | 0.4 | 0.37 |
| 168 h | 1.78 | 0.49 | | 0.4 | 0.4 |
| 312 h | 1.86 | 0.33 | | | 0.22 |
| Acid number (mg KOH/g) | | | | | |
| 0 h | 0.1 | 0.07 | 0.08 | 0.05 | 0.02 |
| 96 h | 0.19 | 0.08 | 0.1 | 0.02 | 0.04 |
| 168 h | 0.32 | 0.1 | 0.3 | 0.07 | 0.03 |
| 312 h | 1.01 | 0.07 | 0.8 | 0.05 | 0.03 |

(C) = comparative example,
(I) = inventive

The results in Table 1 show that the hydrolytic stability of the oil formulations prepared by the method according to the invention is increased even when using lower carbodiimide concentrations. In addition, the temperature must be increased to 80° C. for the compounds of the prior art in order to be able to prepare a solution at all, which is inconvenient and is accompanied by undesirable decomposition processes releasing toxic substances.

TABLE 2

Decrease of the add number at 30° C.:
Comparison between Stabaxol ® MTC (inv) and SXL I (C)
Experimental procedure:
298.5 g of TMP oleate were warmed to 30° C.
Subsequently, either 1.5 g (0.5% by weight) of SXL
MTC or 1.5 g (0.5% by weight) of SXL I powder were
added and the mixture was stirred at 30° C. for 48 h.
A sample was removed at 0, 6, 24 and 48 h respectively
and the acid number thereof was determined.

| t [h] | Experiment I (inv) SXL MTC 0.5% by weight, Add number [mg KOH/g TMP oleate] | Experiment II (C) SXL I 0.5% by weight, Acid number [mg KOH/g TMP oleate] |
|---|---|---|
| 0 | 0.83 | 0.93 |
| 6 | 0.47 | 0.98 |
| 24 | 0.23 | 0.89 |
| 48 | 0.12 | 0.58 |

It was shown that the mixture according to the invention, even at temperatures of 30° C., lead to a distinctly reduced acid number.

What is claimed is:

1. A method for preparing stabilized oil formulations, the method comprising combining bis-o-tolylcarbodiimide with at least one oil at a temperature of 10-30° C.

2. The method according to claim 1, wherein the oil is at least one of an oil based on naphthenic mineral oil and an oil based on esters.

3. The method according to claim 1, wherein the oil is an oil based on esters and comprises at least one of triglycerides, trimethylolpropane esters (TMP) and a pentaerythritol ester.

4. The method according to claim 3, wherein the oil based on esters is rapeseed oil methyl ester.

5. The method according claim 1, wherein the method comprises combining 0.1% to 5% of the carbodiimide with the oil.

6. A method of using the stabilized oil formulation according to claim 1, the method comprising using the oil as at least one of process oils, fuels, heat transfer oils, motor oils, fats, metalworking fluids, turbine and transformer oils.

7. The method according to claim 1, wherein the oil Is trimethylolpropane ester (TMP) of the general formula (II)

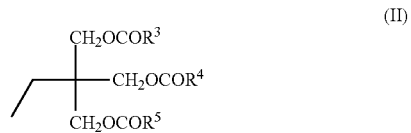

wherein $R^3$, $R^4$ and $R^5$ may each be the same or different and are a linear or branched alkyl group having 5 to 22 carbon atoms.

8. The method according to claim 7, wherein the oil is trimethylolpropane trioleate.

9. The method according to claim 8, wherein the method comprises combining 0.2 to 0.5 wt % of the carbodiimide with the oil at a temperature of 15 to 30° C.

10. The method according to claim 9, further comprising combining at least one of 0.005 to 1.0% by weight of an antioxidant and 0.01 to 2.0% by weight of a metal deactivator with the oil, based on the weight of the oil.

11. The method according to claim 9, further comprising combining at least one of 0.1-0.2% by weight of an antioxidant and 0.1 to 0.2% by weight of a metal deactivator with the oil, based on the weight of the oil, wherein the antioxidant is at least one of bishydroxytoluene, hydroquinone, 4-tert-butylcatechol, naphthol, phenylnaphthylamines, diphenylamines, phenolic thioethers, tocopherols and mixtures thereof, and the metal deactivator is selected from the group consisting of triazoles, tolyltriazoles, dimercaptothiadiazoles and mixtures thereof.

* * * * *